United States Patent
Zhu et al.

(10) Patent No.: US 10,611,789 B2
(45) Date of Patent: Apr. 7, 2020

(54) CRYSTALLINE FORM A OF REBAUDIOSIDE D, AND PREPARATION METHOD AND APPLICATION THEREFOR

(71) Applicant: ZHUCHENG HAOTIAN PHARM CO., LTD, Zhucheng, Weifang, Shandong (CN)

(72) Inventors: Liping Zhu, Shandong (CN); Xuefeng Mei, Shanghai (CN); Ying Huang, Shanghai (CN); Jianrong Wang, Shanghai (CN); Qi Zhang, Shanghai (CN)

(73) Assignee: ZHUCHENG HAOTIAN PHARM CO., LTD, Zhucheng, Weifang, Shandong (CN)

( * ) Notice: Subject to any disclaimer, the term of this patent is extended or adjusted under 35 U.S.C. 154(b) by 0 days.

(21) Appl. No.: 15/747,072

(22) PCT Filed: Jul. 21, 2016

(86) PCT No.: PCT/CN2016/090898
§ 371 (c)(1),
(2) Date: Jan. 23, 2018

(87) PCT Pub. No.: WO2017/012572
PCT Pub. Date: Jan. 26, 2017

(65) Prior Publication Data
US 2018/0371002 A1   Dec. 27, 2018

(30) Foreign Application Priority Data
Jul. 23, 2015   (CN) .......................... 2015 1 0441922

(51) Int. Cl.
| | |
|---|---|
| C07H 15/24 | (2006.01) |
| A23L 2/60 | (2006.01) |
| A23L 33/00 | (2016.01) |
| A61K 47/26 | (2006.01) |
| C07H 15/26 | (2006.01) |
| A23L 27/30 | (2016.01) |
| C07H 1/06 | (2006.01) |
| A23L 2/02 | (2006.01) |
| A61K 47/38 | (2006.01) |
| A61K 31/4402 | (2006.01) |
| A23L 19/00 | (2016.01) |
| C07H 1/08 | (2006.01) |

(52) U.S. Cl.
CPC ............... *C07H 15/24* (2013.01); *A23L 2/02* (2013.01); *A23L 2/60* (2013.01); *A23L 19/00* (2016.08); *A23L 27/30* (2016.08); *A23L 33/00* (2016.08); *A61K 31/4402* (2013.01); *A61K 47/26* (2013.01); *A61K 47/38* (2013.01); *C07H 1/06* (2013.01); *C07H 1/08* (2013.01); *C07H 15/26* (2013.01); *A23L 27/33* (2016.08); *C07B 2200/13* (2013.01)

(58) Field of Classification Search
CPC .......... C07H 15/24; C07H 15/26; C07H 1/06; A61K 47/26; A23L 33/00; A23L 27/33; A23L 27/30; A23L 2/60; C07B 2200/13
See application file for complete search history.

(56) References Cited

U.S. PATENT DOCUMENTS

| | | | | |
|---|---|---|---|---|
| 8,299,224 | B2 * | 10/2012 | Abelyan | C07H 15/24 536/128 |
| 8,501,261 | B2 † | 8/2013 | Markosyan | |
| 2015/0017284 | A1 | 1/2015 | Prakash et al. | |

FOREIGN PATENT DOCUMENTS

| | | |
|---|---|---|
| CN | 102406113 A | 4/2012 |
| CN | 102811627 A | 12/2012 |
| CN | 102894325 A | 1/2013 |
| CN | 103709215 A | 4/2014 |
| CN | 104159908 A | 11/2014 |
| EP | 2480097 A1 † | 8/2012 |
| EP | 2358730 B1 | 1/2014 |
| WO | 2011112892 A1 | 9/2011 |
| WO | 2012082587 A2 | 6/2012 |

* cited by examiner
† cited by third party

*Primary Examiner* — Jonathan S Lau
(74) *Attorney, Agent, or Firm* — Novick, Kim & Lee, PLLC; Bin Lu

(57) ABSTRACT

Provided are crystalline form A of rebaudioside D, and a preparation method and application therefor. In X-ray powder diffraction analysis measured using Cu-K$\alpha$ rays and with $2\theta$ being expressed in degrees, crystalline form A of rebaudioside D has significant characteristic diffraction peaks at least at 4.53, 6.38, 12.76, 13.52, 17.48, 17.96, 20.07 and 22.63. The preparation method is a suspension method, a solvent evaporation method or a cooling method. The preparation method has a simple process, and is convenient to operate. A rebaudioside D crystalline form A product has a good degree of crystallinity, good water solubility, and high chemical stability.

7 Claims, 8 Drawing Sheets

CRYSTALLINE FORM A OF REBAUDIOSIDE D, AND PREPARATION METHOD AND APPLICATION THEREFOR

TECHNICAL FIELD

The present invention relates to the field of sweeteners technology, in particular, to crystalline form A of Rebaudioside D, and preparation method and application therefor.

BACKGROUND

Polymorphism refers to a different solid form (such as a diamond and a graphite) formed from the same elements or molecules spatially arranged in different ways. The difference in arrangement can come from different accumulation ways of space elements or molecules, or different conformational isomers due to the structural flexibility of the molecules themselves, which thereby leads to differences in spatial arrangement. However, such differences in arrangement will lead to different crystal forms with different solubility, physical and chemical stability, reactivity, mechanical stability and morphology.

The changes of the solid state in crystalline drugs or foods may be occurred during processing or storage. This is mainly due to the fact that various process treatments of APIs are usually involved in the preparation process, and the external stimulus is typically from mechanical crushing, grinding, compression moulding or tableting process, freezing, drying, melting and the like. In addition, drugs or food may absorb moisture during storage, interact with oxygen in the air, decompose impurities and interact with excipients and so on.

The changes in the crystalline form can lead to changes in various solid-state chemistry related properties, such as lattice volume, density, viscosity, surface tension, hardness, crystal morphology, color, refractive index, melting point, heat of solution, solubility, dissolution rate, stability, hygroscopicity and chemical reaction performance and so on. Importantly, different crystal forms may lead to changes in drug dissolution, dissolution performance, pharmacokinetics, and bioavailability, thereby affecting the efficacy and safety of drug. Meanwhile, on the food side, different crystal forms may lead to changes in color, morphology, stability and hygroscopicity, which thereby affect the storage conditions, taste and sensory evaluation of food. Therefore, it is of great importance in the process of food and drug research and development to compare the hygroscopicity, chemical stability and workability of different crystal forms, and then select the optimal crystal form.

The structure of Rebaudioside D (RD) is as shown below:

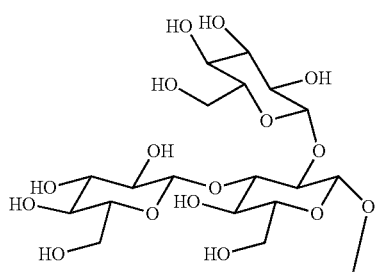

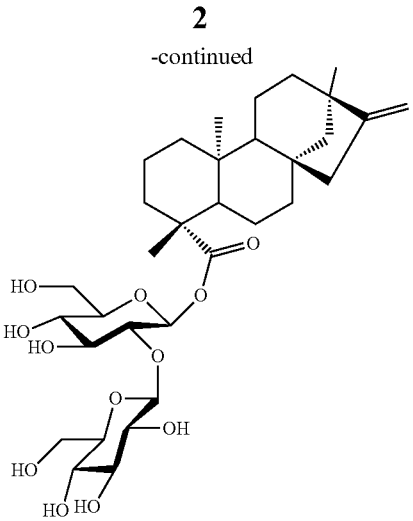

Rebaudioside D (RD), a steviol glycoside compound extracted from *stevia*, is about 200 times as sweet as sucrose and is considered as a potential sweetener. Among the steviol glycoside compound, Rebaudioside A has been widely used as a sweetener in beverage applications but has a problem of bad taste, whereas Rebaudioside D has a better sugar characteristic and more desirable flavor than Rebaudioside A.

A study in the journal of "Journal of Agricultural and Food Chemistry" entitled "Human Psychometric and Taste Receptor Responses to Steviol Glycosides" shows that the sweetness of Rebaudioside D is strongest, and the bitter is weaker compared to Rebaudioside A, Rebaudioside B, Rebaudioside C, Rebaudioside E and Rebaudioside F.

In addition, it is reported in patent of CN 102894325 A that Rebaudioside D can be used to improve the existing sweeteners, especially the taste and flavor of a steviol glycoside in the natural sweeteners. The improved sweetener has a similar taste with sucrose, no bitter and astringency, no artificial synthetic ingredients and energy components are added, and the natural and energy-free characteristics of a steviol glycoside and Rebaudioside A are maintained. However, the low water solubility of Rebaudioside D at room temperature (300 to 450 ppm) limits its use in the food, beverage, flavoring, brewing, pharmaceutical and other industries. Although the preparation and extraction method for Rebaudioside D are reported in CN 104159908 A and CN 103709215 A, respectively, the crystal form of Rebaudioside D has never been reported. Different crystal forms may lead to differences in color, morphology, stability, hygroscopicity and solubility, which thereby affect the storage conditions, taste and sensory evaluation of the food. Different preparation method will make the obtained crystal forms unpredictable. Therefore, it is of great importance to optimize and control the conditions to obtain the optimal crystal form in the development of food and medicine.

There is an urgent need in the art to provide a crystal form of Rebaudioside D with a better property, such as a new crystal form with a good crystallinity, a good water solubility, a high chemical stability. Meanwhile, there is an urgent need to provide a preparation method and a use of the above-mentioned crystal forms.

SUMMARY OF INVENTION

One of the objections of the present invention is to provide a crystal form A of Rebaudioside D with a good crystallinity, a good water solubility, a high chemical stability.

In order to solve the above mentioned technical problem, the technical solution of the present invention is:

A crystal form A of Rebaudioside D, the X-ray powder diffraction analysis of which is obtained using Cu-Kα ray measurment with 2θ values in degrees with an error range of ±1° and the crystal plane spacing d of which is represented by Å and the relative intensity of the diffraction peak of which is expressed as a percentage, which has the following characteristics:

| 2 θ | d | relative intensity % |
|---|---|---|
| 4.53 | 19.5129 | 39.7 |
| 6.38 | 13.8374 | 46.4 |
| 10.37 | 8.5210 | 33.9 |
| 12.76 | 6.9319 | 54.9 |
| 13.52 | 6.5432 | 52.0 |
| 15.11 | 5.8596 | 27.8 |
| 16.45 | 5.3858 | 25.3 |
| 17.48 | 5.0695 | 100.0 |
| 17.96 | 4.9363 | 98.7 |
| 18.36 | 4.8291 | 21.0 |
| 18.64 | 4.7571 | 36.2 |
| 20.07 | 4.4197 | 73.7 |
| 20.49 | 4.3300 | 39.8 |
| 22.63 | 3.9259 | 57.0 |
| 24.18 | 3.6775 | 27.6 |
| 24.79 | 3.5891 | 23.8 |
| 26.19 | 3.4005 | 20.7 |

As an improvement, X-ray powder diffraction analysis of crystal form A obtained using Cu-Kα ray measurement has an obvious characteristic diffraction peak at least at 4.53, 6.38, 12.76, 13.52, 17.48, 17.96, 20.07 and 22.63 of 2θ value expressed as degrees.

As an improvement, the differential scanning calorimetry analysis of crystal form A has a significant endothermic peak at 50° C.-120° C.

As an improvement, the thermogravimetic analysis of crystal form A, decomposition begins at 275±10° C. with a significant weight loss at the beginning of the experiment.

As an improvement, the crystal form A has a dynamic vapor sorption (DVS) pattern as shown in FIG. 4, and the mass percentage of absorbed moisture is 0-3.4% within a relative humidity of 0-40%, the mass percentage of absorbed moisture is 3.4-7.1% within a relative humidity of 40-100%.

As an improvement, the crystal form A has a characteristic peak at least at 3384 cm$^{-1}$, 2946 cm$^{-1}$, 2915 cm$^{-1}$, 1735 cm$^{-1}$, 1660 cm$^{-1}$, 1449 cm$^{-1}$, 1366 cm$^{-1}$, 1074 cm$^{-1}$ in the infrared spectrum.

The second objection of the present invention is to provide a preparation method of the crystal form A of Rebaudioside D, which is simple in process, easy to operate, has good product crystallinity and high stability.

In order to solve the above mentioned technical problem, the technical solution of the present invention is:

A preparation method of the crystal form A of Rebaudioside D, which is a suspension method, a solution volatilization method or a cooling method.

Preferably, the suspension method comprises the following steps:

(1) mixing Rebaudioside D with the solvent for 0.1-48 h at a temperature of zero to the boiling point of the solvent to obtain a suspension solution;

(2) filtering or centrifuging the suspension solution at a temperature of zero to the boiling point of the solvent to obtain a white solid;

(3) drying the white solid at a temperature of zero to the boiling point of the solvent to obtain the crystal form A of Rebaudioside D.

Preferably, the solution volatilization method comprises the following steps:

(1) mixing Rebaudioside D with the solvent for 0.1-48 h at a temperature of zero to the boiling point of the solvent to obtain a suspension solution;

(2) filtering or centrifuging the suspension solution at a temperature of zero to the boiling point of the solvent to obtain a clear solution;

(3) volatilizing the suspension solution of step (1) or the clear solution of step (2) at a temperature of zero to the boiling point of the solvent to obtain the crystal form A of Rebaudioside D.

Preferably, the cooling method comprises the following steps:

(1) mixing Rebaudioside D with the solvent for 0.1-48 h at room temperature to the boiling point of the solvent to obtain a suspension solution;

(2) filtering or centrifuging the suspension solution at room temperature to the boiling point of the solvent to obtain a clear solution;

(3) cooling the suspension solution of step (1) or the clear solution of step (2) to −20-30° C., precipitating a white solid, filtering and drying to obtain the crystal form A of Rebaudioside D.

As an improvement, the Rebaudioside D has a material purity of 50-100%.

As an improvement, the Rebaudioside D and the solvent are mixed by stirring, shaking or vortexing.

As an improvement, the solvent is one or two or more of water, methanol, ethanol, acetonitrile, tetrahydrofuran, acetone, methyl ethyl ketone, ethyl acetate, ethyl formate, 1-propanol and 2-propanol.

As an improvement, the solvent is one or two or more of drying modes of natural drying, air-blast drying, vacuum drying, freeze-drying, airflow drying, microwave drying, infrared drying or high frequency drying.

The third objection of the present invention is to provide a use of the crystal form A of Rebaudioside D in food, beverage and medicine.

As a result of the above technical solutions, the beneficial effects of the present invention are:

The preparation method of the crystal form A of Rebaudioside D provided by the invention has the advantages of simple process, easy operation and more selectivity, and the crystal form A of Rebaudioside D can be prepared by various methods, and the obtained product has a good crystallinity, good water solubility, high chemical stability.

DETAILED DESCRIPTION

Figure 1:
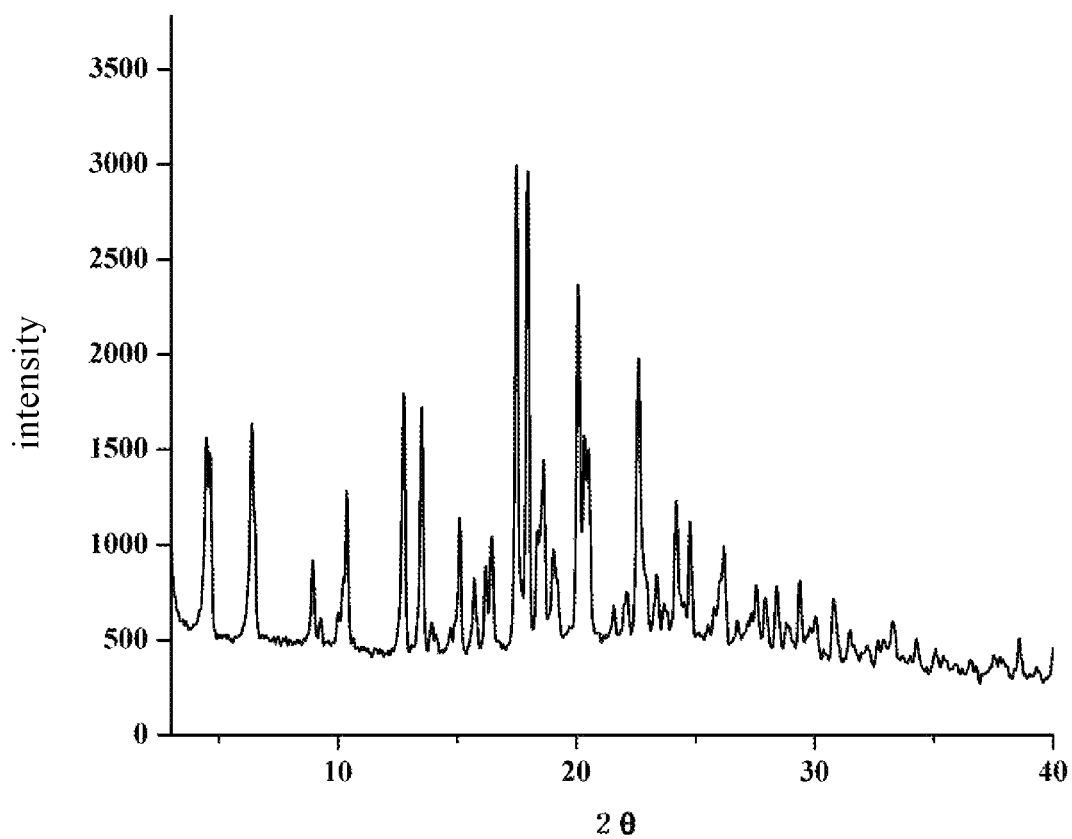
FIG. 1 shows an X-ray powder diffraction (XRPD) pattern of the crystal form A of Rebaudioside D of the present invention.

In order to make the objectives, technical solutions and advantages of the present invention more comprehensible, the present invention is further described in detail below with reference to the accompanying drawings and embodiments. It should be understood that the specific embodiments described herein are only used to explain the present invention, and are not intended to limit the present invention.

EXAMPLE 1

25 g of Rebaudioside D with a material purity of 100% was added to 100 mL of ultrapure water under the condition of 25° C. and placed for 12 h, filtered to give a filtrate and a white solid, the filtrate and the white solid were dried at 25° C. under vacuum, respectively to give the crystal form A of Rebaudioside D.

EXAMPLE 2

25 g of Rebaudioside D with a material purity of 100% was added to 150 mL of 60% ethanol-water (v/v) system under the condition of 25° C. and placed for 12 h, filtered to give a filtrate and a white solid, the filtrate and the white solid were dried at 25° C. under vacuum, respectively to give the crystal form A of Rebaudioside D.

EXAMPLE 3

31.5 g of Rebaudioside D with a material purity of 80% was added to 150 mL of 60% ethanol-water (v/v) system under the condition of 50° C. and placed for 12 h, filtered to give a filtrate and a white solid, the filtrate and the white solid were air-blast dried at 50° C., respectively to give the crystal form A of Rebaudioside D.

EXAMPLE 4

31.5 g of Rebaudioside D with a material purity of 80% was added to 100 mL of 50% ethanol-methanol (v/v) system under the condition of 50° C. and placed for 12 h, filtered to give a filtrate and a white solid, the filtrate and the white solid were air-blast dried at 50° C., respectively to give the crystal form A of Rebaudioside D.

EXAMPLE 5

31.5 g of Rebaudioside D with a material purity of 60% was added to 100 mL of 50% ethanol-methanol (v/v) system under the condition of 60° C. and stirred for 1 h, filtered to give a filtrate and a white solid, the filtrate and the white solid were dried naturally at 50° C., respectively to give the crystal form A of Rebaudioside D.

EXAMPLE 6

31.5 g of Rebaudioside D with a material purity of 60% was added to 100 mL of 50% ethanol-methanol (v/v) system under the condition of 60° C. and swirled for 3 h, filtered to give a filtrate and a white solid, the filtrate and the white solid were dried naturally at 50° C., respectively to give the crystal form A of Rebaudioside D.

EXAMPLE 7

50 g of Rebaudioside D with a material purity of 50% was added to 100 mL of 50% ethanol-methanol (v/v) system under the condition of 60° C. and shaken for 5 h, filtered to give a filtrate and a white solid, the filtrate and the white solid were dried naturally at 50° C., respectively to give the crystal form A of Rebaudioside D.

EXAMPLE 8

25 g of Rebaudioside D with a material purity of 100% was added to 200 mL of ultrapure water under the condition of 90° C. and stirred for 5 h, filtered to give a filtrate and a white solid, the filtrate and the white solid were dried naturally at 50° C., respectively to give the crystal form A of Rebaudioside D.

EXAMPLE 9

25 g of Rebaudioside D with a material purity of 100% was added to 200 mL of ultrapure water under the condition of 90° C. and stirred for 5 h, centrifuged to give a supernatant and a white solid, the supernatant and the white solid were dried naturally at 50° C., respectively to give the crystal form A of Rebaudioside D.

EXAMPLE 10

25 g of Rebaudioside D with a material purity of 100% was added to 300 mL of ultrapure water under the condition of 90° C. and stirred for 5 h to give a suspension solution, the suspension solution was dried naturally at 90° C. to give the crystal form A of Rebaudioside D.

EXAMPLE 11

4 g of Rebaudioside D with a material purity of 100% was added to 600 mL of ultrapure water under the condition of 90° C. and stirred for 5 h, the Rebaudioside D was dissolved completely to give a clear solution, the clear solution was dried naturally at 90° C. to give the crystal form A of Rebaudioside D.

EXAMPLE 12

4 g of Rebaudioside D with a material purity of 100% was added to 600 mL of ultrapure water under the condition of 90° C. and stirred for 5 h, the Rebaudioside D was dissolved completely to give a clear solution, the reaction system was cooled to 25° C., a white solid was precipitated and centrifuged to give a supernatant and a white solid, the supernatant and the white solid were dried naturally at 50° C., respectively to give the crystal form A of Rebaudioside D.

EXAMPLE 13

4 g of Rebaudioside D with a material purity of 100% was added to 600 mL of ultrapure water under the condition of 90° C. and shaken for 24 h, the Rebaudioside D was dissolved completely to give a clear solution, the reaction system was cooled to 30° C., the white solid was precipitated to give a suspension solution, the suspension solution was dried at 30° C. under vacuum to give the crystal form A of Rebaudioside D.

EXAMPLE 14

5 g of Rebaudioside D with a material purity of 100% was added to 600 mL of ultrapure water under the condition of 90° C. and shaken for 24 h, filtered to give a clear solution, the clear solution was cooled to 30° C., a white solid was precipitated and filtrated, the white solid was dried at 30° C. under vacuum to give the crystal form A of Rebaudioside D.

EXAMPLE 15

5 g of Rebaudioside D with a material purity of 100% was added to 600 mL of ultrapure water under the condition of 90° C. and shaken for 24 h, filtered to give a clear solution, the clear solution was cooled to 10° C., a white solid was precipitated and filtrated, the supernatant was dried at 30° C. under vacuum to give the crystal form A of Rebaudioside D.

EXAMPLE 16

25 g of Rebaudioside D with a material purity of 100% was added to 100 mL of ultrapure water under the condition of 0° C. and placed for 48 h, filtrated to give a filtrate and a white solid, the filtrate and the white solid were dried at 25° C. under vacuum, respectively to give the crystal form A of Rebaudioside D.

EXAMPLE 17

4 g of Rebaudioside D with a material purity of 100% was added to 600 mL of acetonitrile under the condition of 90° C. and swirled for 0.1 h, the Rebaudioside D was dissolved completely to give a clear solution, the clear solution was dried naturally at 90° C. to give the crystal form A of Rebaudioside D.

EXAMPLE 18

7 g of Rebaudioside D with a material purity of 100% was added to 600 mL of 2-butanol under the condition of 70° C. and shaken for 30 h, filtrated to give a clear solution, the clear solution was cooled to −20° C., a white solid was precipitated and filtrated, the white solid was dried at 30° C. under vacuum to give the crystal form A of Rebaudioside D.

EXAMPLE 19

6 g of Rebaudioside D with a material purity of 100% was added to 500 mL of ultrapure water under the condition of 80° C. and swirled for 2 h, filtrated to give a clear solution, the clear solution was cooled to 0° C., a white solid was precipitated and filtrated, the white solid was dried at 50° C. under vacuum to give the crystal form A of Rebaudioside D.

The crystal form A of Rebaudioside D prepared in the above examples was subjected to X-ray powder diffraction analysis (XRPD), differential scanning calorimetry (DSC), thermogravimetic analysis (TG), dynamic vapor sorption (DVS), infrared analysis (IR) and so on.

XRPD analysis: a Bruker D8 advance diffractometer from German Brook Instruments Co. LTD was used for detection at room temperature, using Cu-Kα ray ($\lambda$=1.5418 Å) with 2θ angle scanning from 3° to 40° at a scanning speed of 0.2°/second. The analysis results are shown in FIG. 1.

In X-ray powder diffraction patterns of the sample, the diffraction pattern obtained from a specific crystal form is often distinctive. Because of differences in crystallization conditions, particle sizes, relative content of the mixture, and other test conditions, the diffraction pattern may have a preferential orientation effect, resulting in a change in the relative intensities of certain bands (especially at low angles) in the pattern. Therefore, the relative intensity of the diffraction peak is not characteristic to the targeted crystals. The location of the peaks rather than their relative intensities should be noted when determining whether the crystal form is the same as the known crystal form. In addition, it should be noted that when judging whether the crystal form is the same, the overall concept should be kept, because it is not a diffraction line representing a phase, but a set of specific "d-I/I1" data representing a phase. It should also be noted that during the identification of the mixture, because the factors such as the decline in content will cause the lack of part of the diffraction line, there is no need to rely on all the bands observed in the high-purity samples at this time, and even a band may also be characterisitc to the given crystals.

Figure 2:
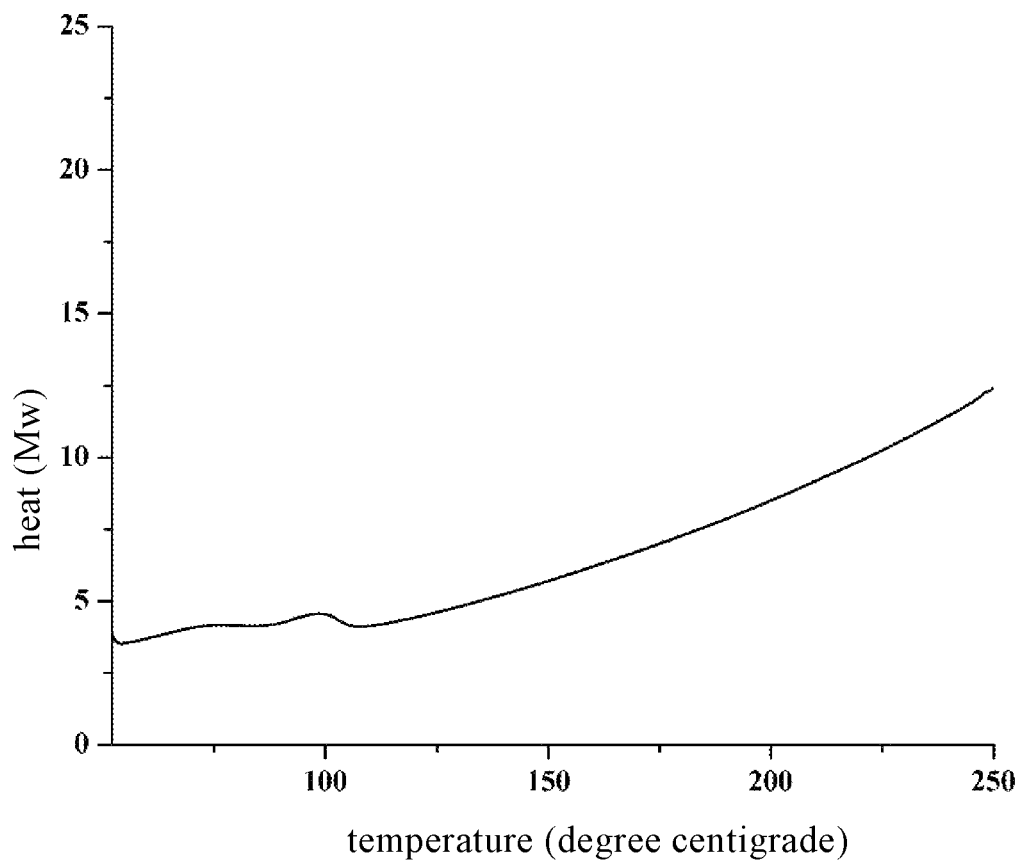
FIG. 2 shows a differential scanning calorimetry (DSC) pattern of the crystal form A of Rebaudioside D of the present invention.

DSC analysis: an American Perkin elmer's DSC 8500 Differential Scanning calorimeter was used for detection. The atmosphere was nitrogen and the heating rate was 10 degrees Celsius/minute. The analysis results are shown in FIG. 2.

Figure 3:
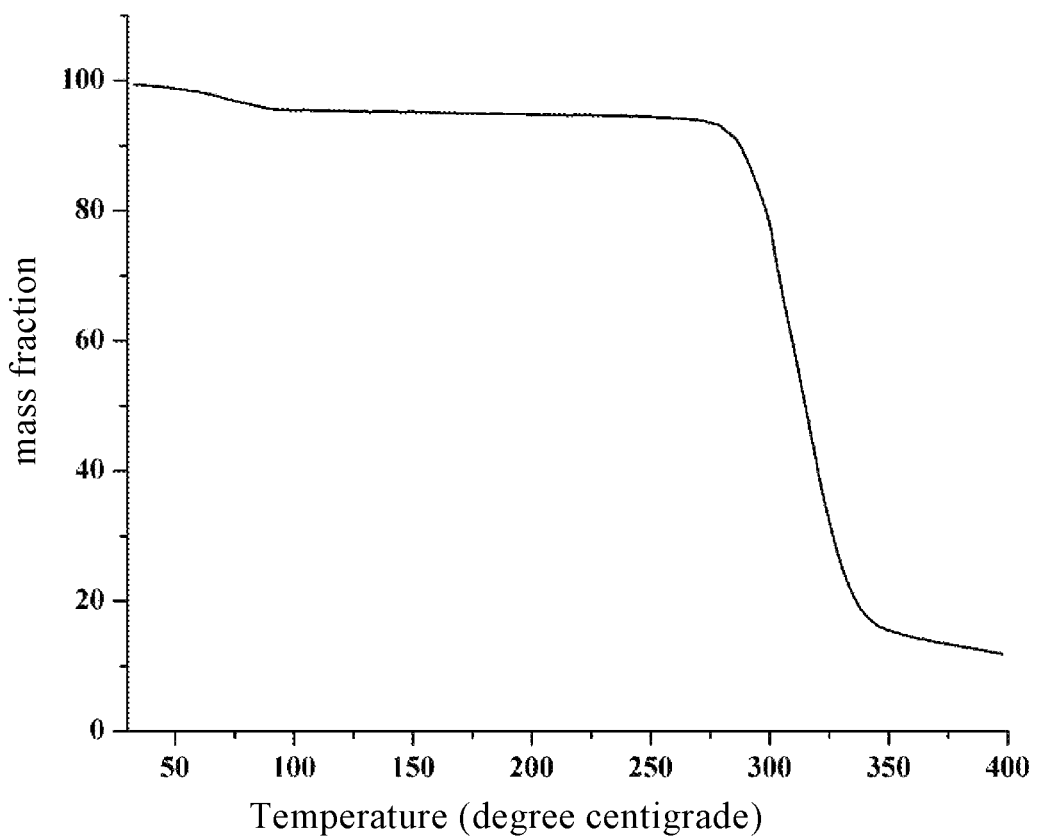
FIG. 3 shows a thermogravimetric analysis (TG) pattern of the crystal form A of Rebaudioside D of the present invention.

TG Analysis: a Netzsch TG 209F3 Thermogravimetric Analyzer from German NETZSCH was used for detection. Temperature range: 30-400° C., scanning rate: 10 K/min, purge gas: 25 mL/min. The analysis results are shown in FIG. 3.

Figure 4:
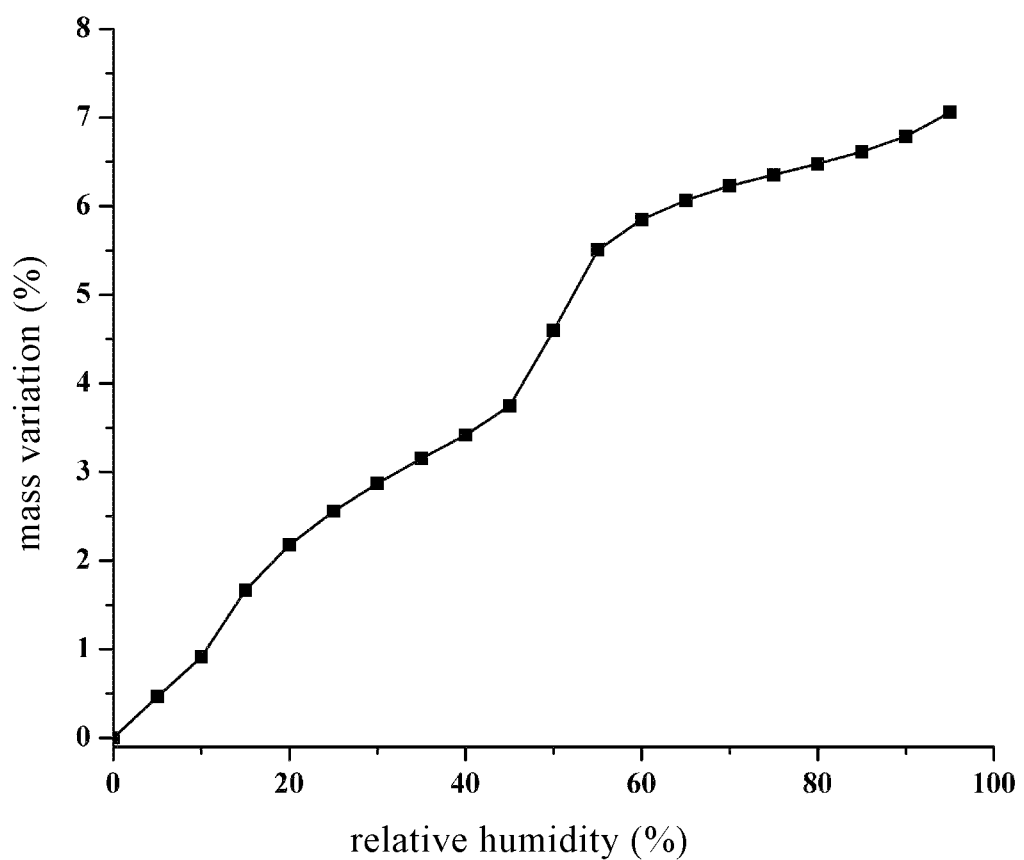
FIG. 4 shows a dynamic vapor sorption (DVS) pattern of the crystal form A of Rebaudioside D of the present invention.

DVS analysis: a DVS Intrinsic Dynamic Moisture Adsorption Device of UK SMS Instrument Company was used for detection. The measuring temperature: 25° C.; the relative humidity: 0-95%. The analysis results are shown in FIG. 4.

Figure 5:
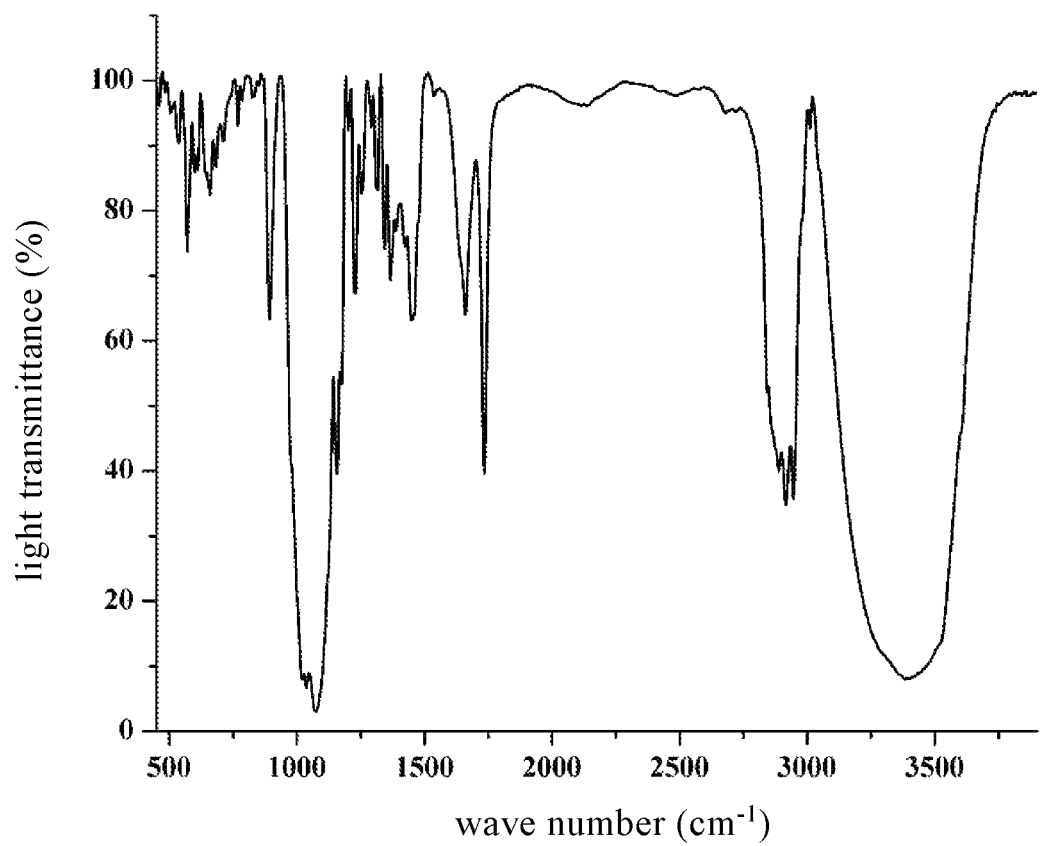
FIG. 5 shows an infrared (IR) spectrogram of the crystal form A of Rebaudioside D of the present invention.

IR analysis: a Nicolet-Magna FT-IR750 Infrared Spectrometer from American Nicolet Corporation was used for detection at room temperature. The detection range was 4000-500 cm$^{-1}$ of wave number. The analysis results are shown in FIG. 5.

Figure 6:
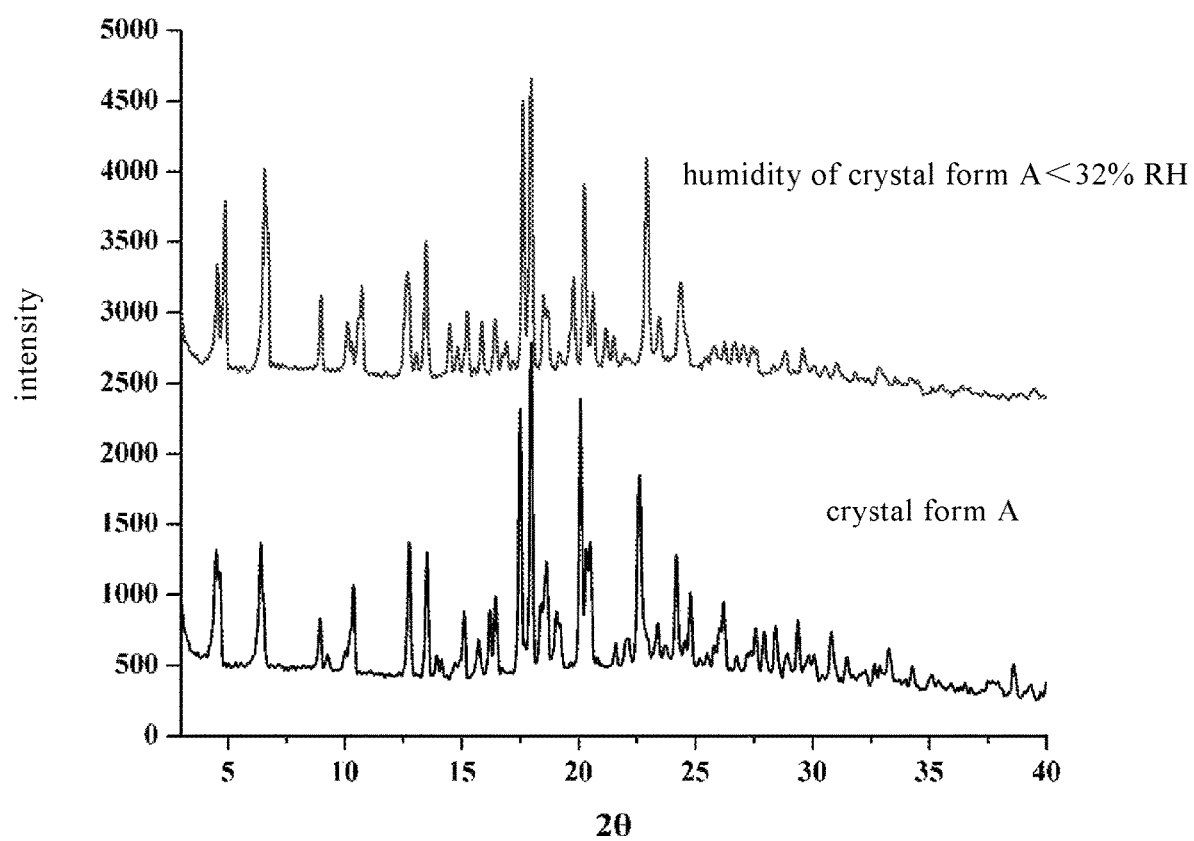
FIG. 6 shows a comparison chart of X-ray powder diffraction (XRPD) of the crystal form A of Rebaudioside D of the present invention under the condition of the relative humidity below 32%.

The crystal form A of Rebaudioside D prepared in the above examples was subjected to XRPD analysis under the conditions of 25° C. and RH≤30%. The analysis results are shown in FIG. 6, and it can be seen from FIG. 6 that the crystal form thereof is unchanged and has a good stability.

Figure 7:
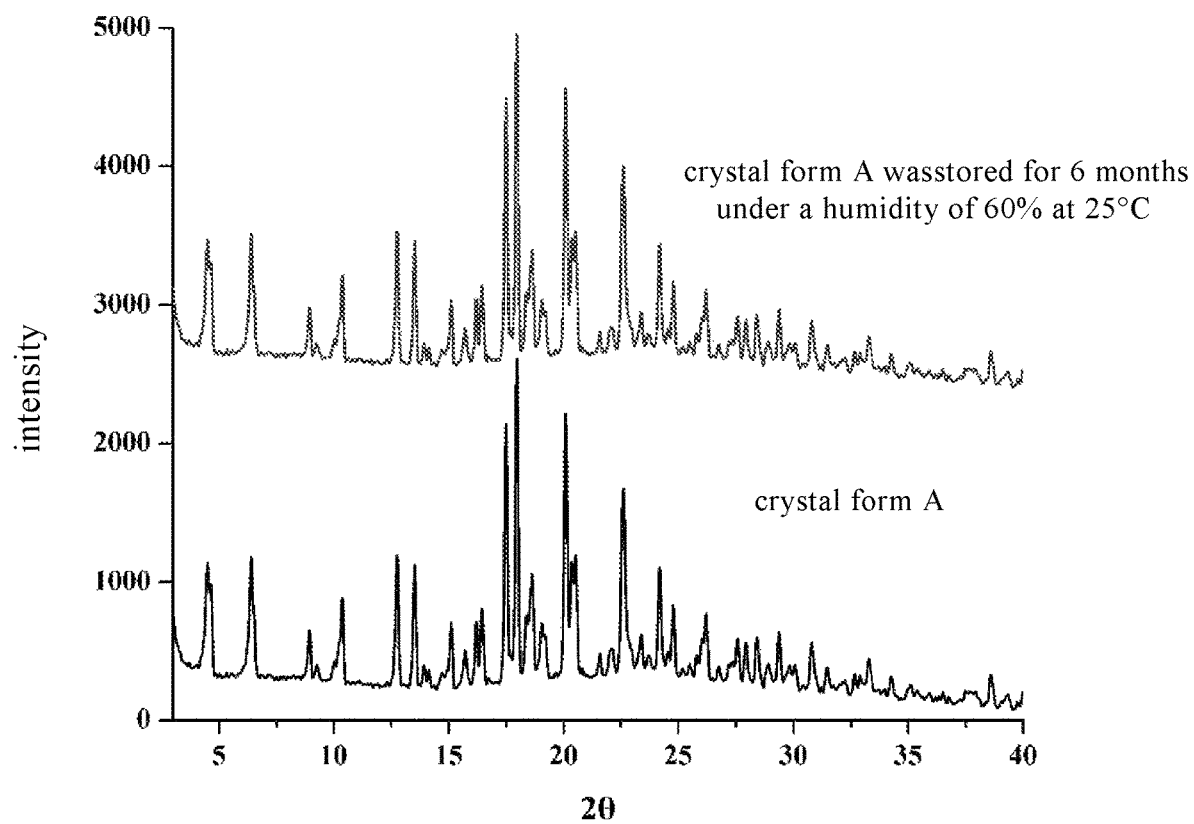
FIG. 7 shows a comparison chart of X-ray powder diffraction (XRPD) of the crystal form A of Rebaudioside D of the present invention stored for six months under the condition of 25° C. and relative humidity of 60%.

The crystal form A of Rebaudioside D prepared in the above examples was stored for 6 months under the conditions of 25° C. and RH≤60%. The analysis results are shown in FIG. 7, and it can be seen from FIG. 7 that the crystal form thereof is unchanged and has a good stability.

Figure 8:
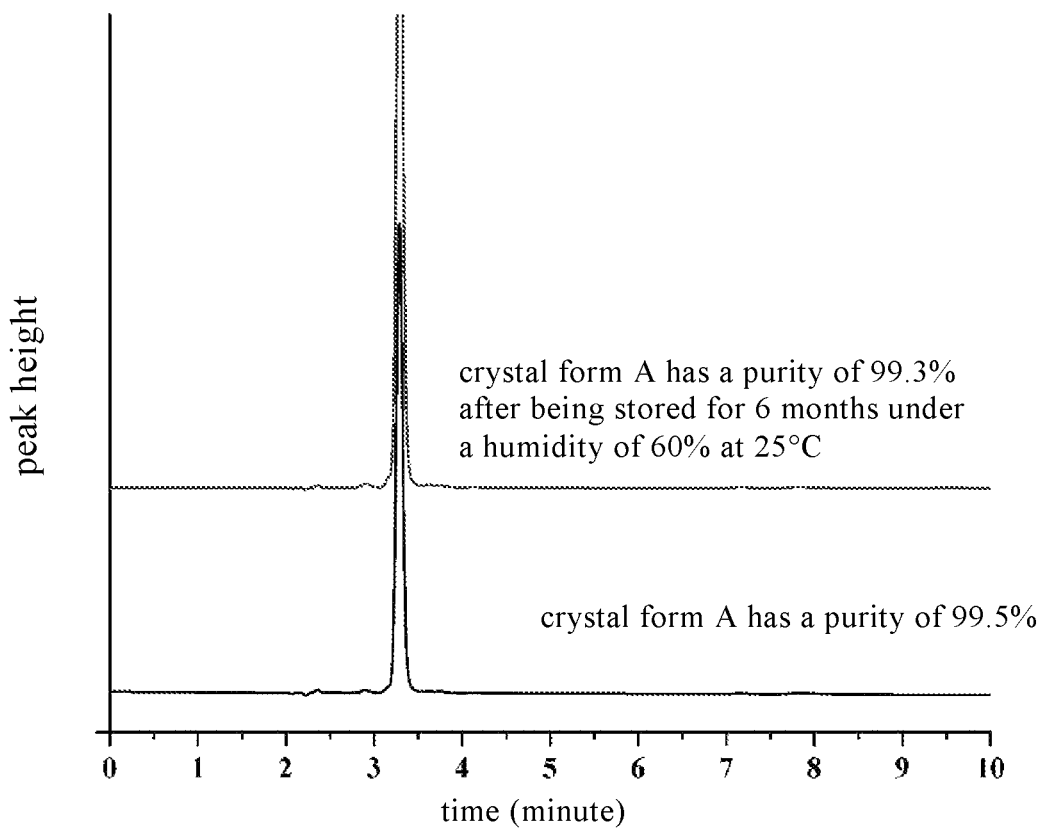
FIG. 8 shows a comparison chart of high performance liquid chromatography (HPLC) of the crystal form A of Rebaudioside D of the present invention stored for six months under the condition of 25° C. and relative humidity of 60%.

HPLC analysis: a 1260 infinity liquid chromatograph from American Agilent Technologies was used for determination. Preparation method for the sample solution: 25-50 mg of the Rebaudioside D sample was accurately weighed, and placed in a 25 ml of volumetric flask, and then a solution of water-acetonitrile (7:3, v/v) was added for dissolution and the volume was set to the scale. The fomulation method for sodium phosphate buffer (specification: 10 mmol/L, pH: 2.6): 2.76 g of sodium dihydrogen phosphate was dissolved in 2 L of water, phosphoric acid was added and the pH was adjusted to 2.6. Chromatographic column: Phenomenex's Luna 5μ C18 (2) 100 A column. Injection volume: 5 μl. Flow rate: 1.0 mL/min. Column temperature: 40° C. Detector: 210 nm of UV detection. Mobile phase: acetonitrile and sodium phosphate buffer (specification: 10 mmol/L, pH: 2.6) at a ratio of 32:68. The analysis results are shown in FIG. 8.

The crystal form A of Rebaudioside D prepared in the above examples has a good chemical stability, and the HPLC analysis shows that its purity is varied less than 0.5% as compared with that of the raw material after six months of storage.

The crystal form A of Rebaudioside D prepared in the above examples has a good reproducibility, and has a good water solubility of about 0.6 mg/mL.

The Rebaudioside D raw materials used in the above examples were supplied by Shandong Zhucheng Haotian Pharmaceutical Co., Ltd.

EXAMPLE 20

A Health Beverage

A health beverage, which consists of the following raw materials: 25 g of medlar, 15 g of *Astragalus membranaceus*, 5 g of walnuts, 1 g of crystal form A of Rebaudioside D, 8 g of Chinese yam and 2 g of Lotus Plumule.

EXAMPLE 21

A Purple Potato Dessert

A purple potato dessert, which consists of the following raw materials: 250 g of purple potato, 20 g of raisin, 20 g of red dates, 5 g of osmanthus, 5 g of lily and 25 g of crystal form A of Rebaudioside D.

EXAMPLE 22

A Medicine for the Treatment of Children's Cold

A purple potato dessert, which consists of the following raw materials: 80 g of acetaminophen, 7 g of pseudoephedrine hydrochloride, 0.3 g of chlorpheniramine maleate, 20 g of starch, 8 g of sodium carboxymethylcellulose, 8 g of crystal form A of Rebaudioside D and 3 g of magnesium stearate.

The foregoing descriptions are merely preferred embodiments of the present invention, and are not used to limit the present invention. Any modifications, equivalent replacements and improvements made within the spirit and principle of the present invention should be included in the protection scope of the present invention.

The invention claimed is:

1. A crystal form A of Rebaudioside D, wherein the crystal form A has characteristic diffraction peaks of X-ray powder diffraction analysis, which are measured by Cu-Kα ray measurement and expressed as 2θ value in degree with an error range of ±1°, and the characteristic diffraction peaks include 3 or more characteristic diffraction peaks selected from the group consisting of: 4.53, 6.38, 12.76, 13.52, 17.48, 17.96, 20.07 and 22.63.

2. The crystal form A of Rebaudioside D of claim 1, wherein the X-ray powder diffraction analysis of the crystal form A obtained using Cu-Kα ray measurement has characteristic diffraction peaks expressed as 2θ value in degree with an error range of ±1°, crystal plane spacings expressed as d in Å and relative intensity of the diffraction peaks expressed as a percentage, which have the following characteristics:

| 2θ | d | relative intensity % |
|---|---|---|
| 4.53 | 19.5129 | 39.7 |
| 6.38 | 13.8374 | 46.4 |
| 10.37 | 8.5210 | 33.9 |
| 12.76 | 6.9319 | 54.9 |
| 13.52 | 6.5432 | 52.0 |
| 15.11 | 5.8596 | 27.8 |
| 16.45 | 5.3858 | 25.3 |
| 17.48 | 5.0695 | 100.0 |
| 17.96 | 4.9363 | 98.7 |
| 18.36 | 4.8291 | 21.0 |
| 18.64 | 4.7571 | 36.2 |
| 20.07 | 4.4197 | 73.7 |
| 20.49 | 4.3300 | 39.8 |
| 22.63 | 3.9259 | 57.0 |
| 24.18 | 3.6775 | 27.6 |
| 24.79 | 3.5891 | 23.8 |
| 26.19 | 3.4005 | 20.7 |

3. The crystal form A of Rebaudioside D of claim 1, wherein the crystal form A has one or more characteristics selected from the group consisting of:
   (1) the crystal form A has a differential scanning calorimetry analysis pattern substantially as shown in FIG. 2;
   (2) the crystal form A has a thermogravimetric analysis pattern substantially as shown in FIG. 3;
   (3) the crystal form A has a dynamic vapor sorption pattern substantially as shown in FIG. 4; and/or
   (4) the crystal form A has a infrared spectrogram substantially as shown in FIG. 5.

4. The crystal form A of Rebaudioside D of claim 1, wherein the crystal form A has characteristic diffraction peaks of X-ray powder diffraction analysis, which are measured by Cu-Kα ray measurement and expressed as 2θ value in degree with an error range of ±0.1°.

5. A food, beverage or pharmaceutical product, which contains a crystal form A of Rebaudioside D according to claim 1 as a sweetener.

6. A preparation method for the crystal form A of Rebaudioside D, wherein the preparation method is a suspension method, a solution volatilization method or a cooling method, wherein the suspension method comprises the following steps:
   (1) mixing Rebaudioside D with the solvent for 0.1-48 h at a temperature of 0° C. to the boiling point of the solvent to obtain a suspension solution; wherein the solvent is selected from the group consisting of water, methanol, ethanol, acetonitrile, tetrahydrofuran, acetone, methyl ethyl ketone, ethyl acetate, ethyl formate, 1-propanol, 2-propanol, and a combination thereof;
   (2) filtering or centrifuging the suspension solution at a temperature of 0° C. to the boiling point of the solvent to obtain a white solid; and
   (3) drying the white solid at a temperature of 0° C. to the boiling point of the solvent to obtain the crystal form A of Rebaudioside D, wherein the solution volatilization method comprises the following steps:
   (1) mixing Rebaudioside D with the solvent for 0.1-48 h at a temperature of 0° C. to the boiling point of the solvent to obtain a suspension solution; wherein the solvent is selected from the group consisting of water, methanol, ethanol, tetrahydrofuran, acetonitrile, and a combination thereof;

(2) filtering or centrifuging the suspension solution at a temperature of 0° C. to the boiling point of the solvent to obtain a clear solution; and (3) volatilizing the suspension solution of step (1) or the clear solution of step (2) at a temperature of 0° C. to the boiling point of the solvent to obtain the crystal form A of Rebaudioside D, and wherein the cooling method comprises the following steps:

(1) mixing Rebaudioside D with the solvent for 0.1-48 h at room temperature to the boiling point of the solvent to obtain a suspension solution; wherein the solvent is selected from the group consisting of water, methanol, ethanol, 2-butanol, and a combination thereof;

(2) filtering or centrifuging the suspension solution at room temperature to the boiling point of the solvent to obtain a clear solution; and (3) cooling the suspension solution of step (1) or the clear solution of step (2) to −20-30° C., precipitating a white solid, filtering and drying to obtain the crystal form A of Rebaudioside D.

7. The preparation method for the crystal form A of Rebaudioside D of claim 6, wherein the drying is one or two or more of drying modes of natural drying, air-blast drying, vacuum drying, freeze-drying, airflow drying, microwave drying, infrared drying or high frequency drying, wherein the natural drying means dried naturally at 50° C.

* * * * *